United States Patent
Peng et al.

(10) Patent No.: US 10,234,366 B2
(45) Date of Patent: Mar. 19, 2019

(54) ROTATABLE SAMPLE INTRODUCING DEVICE

(71) Applicant: Nuctech Company Limited, Beijing (CN)

(72) Inventors: Hua Peng, Beijing (CN); Yi Xiao, Beijing (CN); Yuanjing Li, Beijing (CN); Jianhua Liu, Beijing (CN); Wangyang Wu, Beijing (CN); Haichao Zhou, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 297 days.

(21) Appl. No.: 14/982,535

(22) Filed: Dec. 29, 2015

(65) Prior Publication Data

US 2016/0187242 A1 Jun. 30, 2016

(30) Foreign Application Priority Data

Dec. 29, 2014 (CN) .......................... 2014 1 0837799

(51) Int. Cl.
*G01N 1/02* (2006.01)
*G01N 1/40* (2006.01)
(Continued)

(52) U.S. Cl.
CPC ............ *G01N 1/4022* (2013.01); *B01L 3/502* (2013.01); *B01L 7/00* (2013.01); *B01L 2200/026* (2013.01);
(Continued)

(58) Field of Classification Search
CPC .............................................. G01N 2001/028
See application file for complete search history.

(56) References Cited

U.S. PATENT DOCUMENTS 2,983,436 A * 5/1961 Greenwald ............... G07F 9/06
232/1 R
3,091,967 A * 6/1963 Hurdlow .................. G01N 1/04
73/864.71
(Continued)

FOREIGN PATENT DOCUMENTS

CN 101461033 A 6/2009
CN 101644645 A 2/2010
EP 1 596 180 A2 11/2005

OTHER PUBLICATIONS

Extended European Search Report dated Jun. 25, 2018 received from the European Patent Office in related Application No. EP 15875063.8.

*Primary Examiner* — Robert R Raevis

(74) *Attorney, Agent, or Firm* — Scully, Scott, Murphy & Presser, P.C.

(57) ABSTRACT

The present disclosure provides a rotatable sample introducing device for a trace detecting instrument including: a rotating rod, a sample introducing body and a rotating rod bracket, wherein the sample introducing body may be positioned inside the rotating rod bracket, the rotating rod passing through the rotating rod bracket and the sample introducing body may be fixed to the sample introducing body by a fastener, and the rotating rod may be rotatable. The rotatable sample introducing device for the trace detecting instrument provided by the disclosure has the following advantages in comparison with the prior art: simple structure, convenient operation, lower requirement for machine process, easy maintenance in later period and low cost.

7 Claims, 3 Drawing Sheets

(51) Int. Cl.
*B01L 3/00* (2006.01)
*B01L 7/00* (2006.01)

(52) U.S. Cl.
CPC . *B01L 2300/0825* (2013.01); *B01L 2300/126* (2013.01)

(56) References Cited

U.S. PATENT DOCUMENTS

| | | | | |
|---|---|---|---|---|
| 3,554,039 | A * | 1/1971 | Braun | G01T 7/02 15/97.1 |
| 4,848,165 | A * | 7/1989 | Bartilson | G01N 1/04 73/864.71 |
| 7,357,044 | B2 * | 4/2008 | Sleeman | G01N 1/02 73/863.12 |
| 2005/0081655 | A1 * | 4/2005 | Fine | G01N 1/02 73/864.71 |
| 2006/0042407 | A1 * | 3/2006 | Napoli | G01N 27/622 73/863.12 |
| 2007/0209453 | A1 * | 9/2007 | Akinbo | G01N 1/40 73/864.71 |
| 2011/0290041 | A1 * | 12/2011 | Wang | G01N 27/622 73/863.11 |

* cited by examiner

ROTATABLE SAMPLE INTRODUCING DEVICE

CROSS-REFERENCE TO RELATED APPLICATIONS

This application is based upon and claims priority to Chinese Patent Application No. 201410837799.X, filed on Dec. 29, 2014, which is incorporated herein by reference in its entirety.

TECHNICAL FIELD

The disclosure relates to the detection field, and more particularly, to a rotatable sample introducing device for a trace detecting instrument.

BACKGROUND

Generally, the operation of a sample introducing device of a trace detecting instrument in the prior art includes inserting an exterior test paper into a sample introducing device after being wiped. Sampling and introducing are separated during the whole processes, which requires a high demand on the thickness and width of the test paper adapted to the sample introducing device and the operation of inserting paper. If a design deviation exists at a paper inserting opening of the sample introducing device or an angle deviation exists during assembly, it will easily cause paper jams or difficulties in paper inserting. Moreover, it is difficult to remove a test paper that is damaged and remains in the sample introducing device, such that a sample detecting effect is influenced and the difficulty of later maintenance is increased. In addition, due to a high accuracy requirement of machine process for the sample introducing device in the prior art, it is hard to process and a high cost is also a problem.

SUMMARY

The disclosure provides a rotatable sample introducing device for a trace detecting instrument to solve the technical problems incurred by high requirements and costly manufacture for the sample introducing device.

In order to solve above technical problems, the present disclosure provides a rotatable sample introducing device for a trace detecting instrument including: a rotating rod, a sample introducing body and a rotating rod bracket, wherein the sample introducing body may be positioned within the rotating rod bracket, the rotating rod, which passes through the rotating rod bracket and the sample introducing body, may be fixed to the sample introducing body by a fastener, and the rotating rod is rotatable.

Further, the rotation of the rotating rod may enable a sample on the sample introducing body to be heated and volatilized by a heater fixed on the rotating rod bracket.

Further, the fastener may be one or more fastening screws.

Further, side surfaces of the sample introducing body may be curved surfaces.

Further, the side surfaces of the sample introducing body may be polygonal.

Further, the sample may be directly wiped onto a surface of the sample introducing body.

Further, the surface of the sample introducing body may be covered by a test paper and the sample may be wiped onto a surface of the test paper.

Further, holes, which correspond to the fastening screws in quantity and size, may be provided on both ends of the test paper, respectively, the fastener is one or more fastening screws, and the test paper may surround a peripheral surface of the sample introducing body and fixed by the fastening screws through the holes on both ends.

Further, the heater may be a heater plate.

Further, the heater may include a through hole.

Further, the sample may move into a detection zone through the through hole of the heater after being heated and volatilized.

Therefore, the rotatable sample introducing device for the trace detecting instrument according to the disclosure has the following advantages in comparison with the prior art: simple structure, convenient operation, lower requirement for machine process, easy maintenance in later period and low cost.

BRIEF DESCRIPTION OF THE DRAWINGS

In order to explain the technical solutions in the present embodiments or in the prior art more clearly, accompanying drawings required in the description of the present embodiments or prior art will be briefly described. Obviously, accompanying drawings are just some embodiments of the present disclosure, while other drawings may be obtained by those skilled in the art according to these drawings, without paying out any creative work.

DETAILED DESCRIPTION

Figure 1:
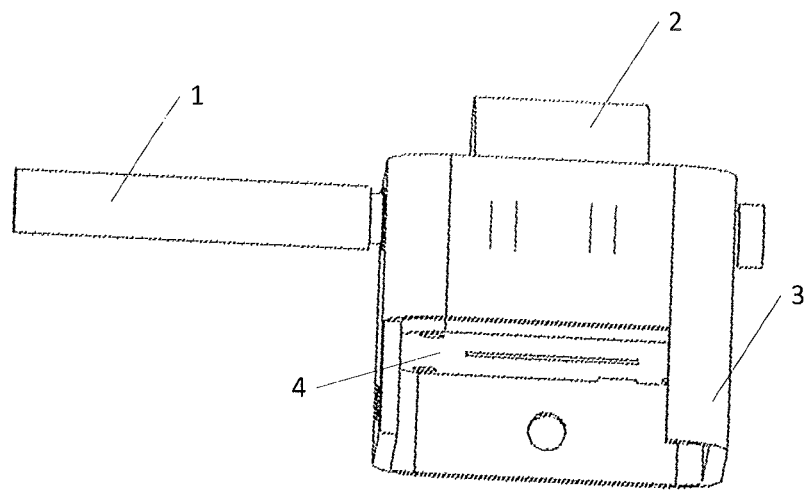
FIG. 1 is a basic structural schematic diagram of a rotatable sample introducing device for a trace detecting instrument according to an embodiment of the disclosure.

The technical solution of the present disclosure will now be described clearly and completely in conjunction with the accompanying drawings of embodiments of the present disclosure so as to make the objects, technical solutions and advantages of the embodiments of the present disclosure more clearly. Obviously, the embodiments described do not represent all but some embodiments. Other embodiments obtained by those skilled in the art without paying out any creative work will fall within the scope protected by the present disclosure.

With reference to FIGS. 1-6, the present disclosure provides a rotatable sample introducing device for a trace detecting instrument.

The rotatable sample introducing device includes a rotating rod 1, a sample introducing body 2 and a rotating rod bracket 3, wherein the sample introducing body 2 is positioned inside the rotating rod bracket 3, the rotating rod 1, which passes through the rotating rod bracket 3 and the sample introducing body 2, is fixed to the sample introducing body 2 by a fastener 5. The rotating rod 1 is rotatable.

Optionally, the rotation of the rotating rod 1 enables a sample on the sample introducing body 2 to be heated and volatilized by a heater 4 fixed on the rotating rod bracket 3.

Figure 2:
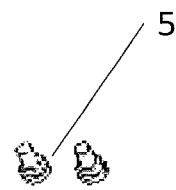
FIG. 2 is a schematic diagram of a fastener according to an embodiment of the disclosure.
Figure 3:
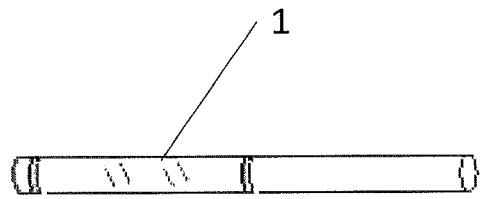
FIG. 3 is a schematic diagram of a rotating rod according to an embodiment of the disclosure.

Optionally, as shown in FIG. 2, the fastener 5 may be one or more fastening screws, to which the screw holes on the rotating rod 1 correspond in quantity and size, as shown in FIG. 3.

Figure 4:
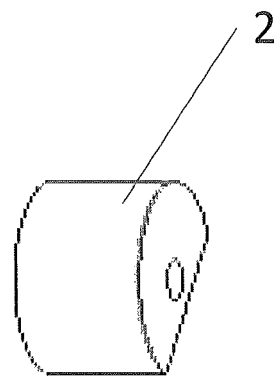
FIG. 4 is a schematic diagram of a sample introducing body according to an embodiment of the disclosure.

Optionally, as shown in FIG. 4, the side surfaces of the sample introducing body 2 may be curved surfaces, for example, arc surfaces. Certainly, the sample introducing body 2 may also be other shapes, for example, polygonal and the like, as long as a well cooperation between sample introducing body 2 and the heater 4 is satisfied when the sample introducing body 2 is heated by the heater.

Among others, sampling may be executed in various ways by the sample introducing body 2. In other words, the sample may either be directly wiped onto a surface of the sample introducing body 2 acting as a sampler, or be wiped onto a surface of the test paper covering the surface of the sample introducing body 2.

When the surface of the sample introducing body 2 is covered with a test paper, the test paper may surround the whole side surfaces of the sample introducing body 2 and may be fixed by the fastener 5. When the fastener 5 is a fastening screw, holes corresponding to the fastening screws 5 in quantity and size may be provided on both ends of the test paper, respectively, such that the test paper surrounds a peripheral surface of the sample introducing body 2 and is fixed by the fastening screws 5 through the holes on both ends.

Figure 5:
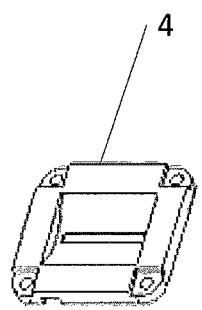
FIG. 5 is a schematic diagram of a heater according to an embodiment of the disclosure.
Figure 6:
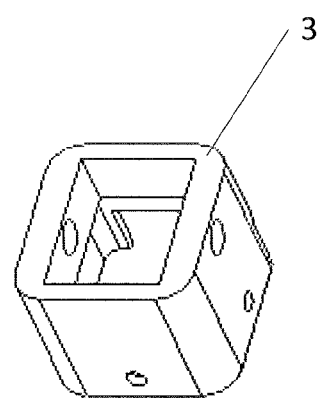
FIG. 6 is a schematic diagram of a rotating rod bracket according to an embodiment of the disclosure.

Optionally, the heater 4 may be a heater plate, as shown in FIG. 5, which is fixed on an end of the rotating rod bracket 3 of FIG. 6.

Optionally, the heater 4 may comprise a through hole or a slit.

Optionally, when the rotatable sample introducing device of the embodiment of the present disclosure is applied into a trace detecting instrument, the sample may move into a detection zone through the through hole of the heater 4 and a heating film located on the trace detecting instrument after being heated and volatilized by the heater 4.

In the embodiment of the present disclosure, the sampling introduction body 2 may be rotated by 180° together with the rotating rod 1 which is fixed to the sampling introduction body 2 by the fastener 5 after sampling is done on the curve surface of the sampling introduction body 2, such that the curve surface faces downward. The sample is volatilized by the heating of the heater 4 and moves into the detection zone to be separated.

Among others, the sample introducing device for the trace detecting instrument of the present disclosure is separable from the trace detecting instrument. The sample introducing device may be separately taken off to sample if used on a large-scale detecting instrument, while it is unnecessary to be taken off if used on a small portable one.

Therefore, the rotatable sample introducing device for the trace detecting instrument provided by the disclosure has the following advantages in comparison with the prior art: simple structure, convenient operation, lower requirement for machine process, easy maintenance in later period and low cost.

Finally, it should be noted that the embodiment disclosed above should be considered in descriptive sense only and not intended to limit. Although the present disclosure has been disclosed in detail with reference to the previous embodiment, those skilled in the art should understand that the technical solution recorded in each previous embodiment may be modified, or some technical features therein may be equivalently substituted; however, these modifications or substitutions will not result in the nature of corresponding technical solutions departing from the spirit and scope of the technical solutions in the embodiments of the present disclosure.

What is claimed is:

1. A rotatable sample introducing device for a trace detecting instrument, comprising:
    a rotating rod bracket having respective openings on opposite sides, a heater being fixed to the rotating rod bracket and the heater having a through hole;
    a rotating rod configured to rotate; and
    a sample introducing body,
    positioned inside the rotating rod bracket, the sample introducing body having respective openings on opposite sides,
    wherein the rotating rod extends through the respective openings of the rotating rod bracket and the respective openings of the sample introducing body, the rotating rod
    is fixed to the sample introducing body by a fastener,
    wherein the rotation of the rotating rod enables a sample on the sample introducing body to be heated and volatilized by the heater, and
    wherein the sample moves into a detection zone through the through hole of the heater after being heated and volatilized.

2. The rotatable sample introducing device according to claim 1, wherein the fastener is one or more fastening screws.

3. The rotatable sample introducing device according to claim 1, wherein side surfaces of the sample introducing body are curved or polygonal surfaces.

4. The rotatable sample introducing device according to claim 1, wherein the sample is directly wiped onto a surface of the sample introducing body.

5. The rotatable sample introducing device according to claim 1, wherein a surface of the sample introducing body is covered by a test paper, and the sample is wiped onto a surface of the test paper.

6. The rotatable sample introducing device according to claim 5, wherein the fastener is one or more fastening screws, holes, which correspond to the fastening screws in quantity and size, are provided on both ends of the test paper, respectively, and the test paper surrounds a peripheral surface of the sample introducing body and is fixed by the fastening screws through the holes on both ends.

7. The rotatable sample introducing device according to claim 1, wherein the heater is a heater plate.

* * * * *